(12) United States Patent
Hogeland

(10) Patent No.: US 7,296,479 B2
(45) Date of Patent: Nov. 20, 2007

(54) FORCE SENSOR AND LAPAROSCOPIC INSTRUMENT PROVIDED WITH SUCH A FORCE SENSOR

(75) Inventor: Mattijs Hogeland, Amsterdam (NL)

(73) Assignee: Academisch Medisch Centrum, Amsterdam (NL)

(*) Notice: Subject to any disclaimer, the term of this patent is extended or adjusted under 35 U.S.C. 154(b) by 81 days.

(21) Appl. No.: 11/356,554

(22) Filed: Feb. 16, 2006

(65) Prior Publication Data
US 2006/0201262 A1    Sep. 14, 2006

Related U.S. Application Data

(63) Continuation of application No. PCT/NL2004/000585, filed on Aug. 20, 2004.

(30) Foreign Application Priority Data
Aug. 27, 2003  (NL)  .................................. 1024171

(51) Int. Cl.
G01L 1/24 (2006.01)
(52) U.S. Cl. ...................................................... 73/800
(58) Field of Classification Search ................. 73/800, 73/849
See application file for complete search history.

(56) References Cited

U.S. PATENT DOCUMENTS

| | | | |
|---|---|---|---|
| 4,674,900 A | | 6/1987 | Erzsebet |
| 4,972,073 A | * | 11/1990 | Lessing .................. 250/227.16 |
| 5,479,828 A | * | 1/1996 | Bonniau et al. ............... 73/800 |
| 6,836,352 B2 | * | 12/2004 | Fitzpatrick et al. ......... 359/291 |
| 6,856,448 B2 | * | 2/2005 | Fitzpatrick et al. ......... 359/291 |
| 7,112,023 B1 | * | 9/2006 | Tardif .......................... 410/96 |
| 2006/0201262 A1 | * | 9/2006 | Hogeland .............. 73/862.625 |

FOREIGN PATENT DOCUMENTS

| | | |
|---|---|---|
| DE | 4410463 | 9/1995 |
| DE | 19523756 | 1/1997 |

OTHER PUBLICATIONS

Sukthankar, S. M., et al., "Towards Force Feedback in Laparoscopic Surgical Tools", *Proceedings of the 16th Annual International Conference of the IEEE Engineering in Medicine and Biology Society. Engineering Advances New Opportunities for Biomedical Engineers*, vol. 2, (1994), 1041-1042.

* cited by examiner

*Primary Examiner*—Max Noori
(74) *Attorney, Agent, or Firm*—Jeffrey D. Myers; Samantha A. Updegraff; Peacock Myers, P.C.

(57) ABSTRACT

A force sensor comprising a deformable body and a detector coupled to this deformable body for measuring a force brought to bear on the deformable body, wherein the detector comprises a light conductor and, disposed close to an end of the light conductor and coupled with the body a position-variable mirror, the light reflection of which depends on the position of the mirror.

7 Claims, 1 Drawing Sheet

FORCE SENSOR AND LAPAROSCOPIC INSTRUMENT PROVIDED WITH SUCH A FORCE SENSOR

Figure 1:
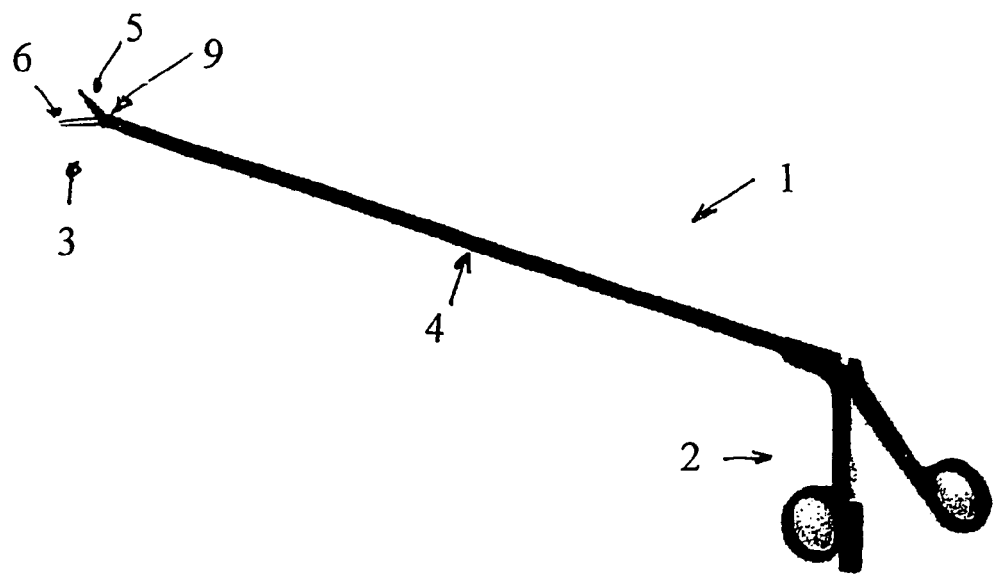

This application is a continuation of PCT/NL04/00585 filed Aug. 20, 2004.

The invention relates to a force sensor comprising a deformable body and a detector coupled to this deformable body for measuring a force brought to bear on the deformable body.

Such a force sensor is known from various technical applications. As a rule, the known force sensor is comprised of a strain gauge that is provided on the deformable body and of which the tension is measured. Depending on the deformation undergone by the body, the strain gauge gives out a voltage that is considered to be indicative of the force brought to bear on the body. The problem is that in essence not the force is measured but a moment on the body. In the prior art therefore, the measurement performed by the force sensor is partly determined by the place where the force is brought to bear on the body.

It is an object of the invention to provide a force sensor that irrespective of the position of force application on the body will provide a force-dependent signal.

From DE-A-195 23 756 an opto-electrical sensor is known, which comprises a deformable body and a detector coupled with this deformable body for measuring a force brought to bear on that body wherein the detector comprises a light conductor and, disposed close to an end of the light conductor and coupled with the body a position-variable mirror, the light reflection of which depends on the position of the mirror.

The force sensor according to the invention is characterised in that the deformable body comprises a channel extending longitudinally in the body, exiting on both sides in a first and second recess, each of which in the direction at right angles to the channel, are wider than the channel. This provides a number of micro-scale pivoting points in the body such that, depending on the force, the deflection of the mirror will as much as possible be a linear one.

In order for the force sensor to function well, it is further desirable that the light conductor be a glass fibre stationarily incorporated in the body.

Desirably, the light conductor is designed for conducting light to and from the mirror. In order to effectively utilise this, a beam-splitter may be placed at the beginning of the light conductor for separating the light being conducted to the mirror from the light coming from the mirror.

The light conductor is preferably at least partly incorporated in the channel and exits in the channel close to the above-mentioned mirror.

It has been shown to be advisable for the mirror to be placed in the channel, supported by a mirror holder mounted on a recess wall away from the light conductor.

For accuracy and precision of the force measurement it is further desirable for the mirror holder to have a length such that when a force is brought to bear on the deformable body, the light-reflecting surface of the mirror will undergo a substantially linear deflection.

A favourable aspect of the force sensor according to the invention is that it possesses a processing organ for determining a ratio between a first amount of light conducted by the light conductor to the mirror, and a second amount of light conducted by the light conductor from the mirror, and that this ratio serves as indication of the force brought to bear on the body.

The invention is also embodied in a laparoscopic instrument comprising a proximal handgrip, a distal grasper, and a tube extending between the handgrip and the grasper, containing coupling means for operating the grasper with the aid of the handgrip, wherein the grasper has an upper jaw and a lower jaw.

The use of such a laparoscopic instrument is known in surgery and it serves for performing operations without needing to completely open up the patient.

A disadvantage of the known laparoscopic instrument is that in order to operate this instrument, much surgical experience is required due to a great deal of friction in the coupling means for the control between handgrip and grasper. As a result, the user of the known laparoscopic instrument does not receive a physical feedback signal indicative for the force exerted with the grasper.

In order to facilitate this, it is proposed in accordance with the invention that the upper jaw and/or the lower jaw be provided with a channel extending longitudinally in the body, exiting at both sides in a first and a second recess, each of which is in the direction at right angles to the channel wider than the channel, and that an end of a light conductor is situated in the channel, close to which a mirror is provided whose position depends on the force exerted on the upper jaw and/or the lower jaw, and that the light reflection of the mirror is dependent on this position.

With such a laparoscopic instrument it is possible to provide the user with a signal he can feel and that corresponds to the force exerted with the grasper.

To this end the laparoscopic instrument according to the invention is further preferably characterised in that the same possesses a processing organ for determining a ratio between a first amount of light conducted by means of the light conductor to the mirror, and a second amount of light conducted by means of the light conductor from the mirror, and that this ratio is indicative of the force brought to bear on the body, and in that an actuator is connected to the processing organ that operates the handgrip to provide a signal that can be felt, which is dependent on said force.

It is further desirable for the light conductor to be a glass fibre stationarily incorporated in the upper jaw and/or the lower jaw, and for the light conductor to be designed for conducting light to and from the mirror.

It is further desirable for the mirror to be disposed in the channel and to be supported by a mirror holder mounted on a recess wall away from the light conductor. It is further advantageous for the mirror holder to have a length such that when a force is exerted on the upper jaw or lower jaw, the light-reflectinq surface of the mirror undergoes a substantially linear deflection. This enables the laparoscopic instrument according to the invention to optimally meet the requirements of precision and reliability.

Hereinbelow the invention will be further elucidated by way of a non-limiting exemplary embodiment and with reference to the drawing.

The drawing shows in:

FIG. 1 a laparoscopic instrument and in

Figure 2:
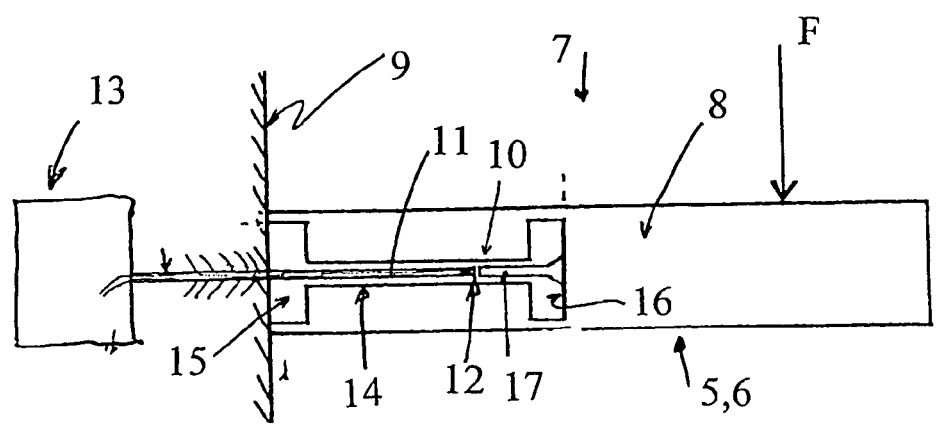

FIG. 2 a schematic illustration of a force sensor such as may be incorporated in a lower jaw or upper jaw of a laparoscopic instrument according to FIG. 1.

Similar parts in the figures carry identical reference numerals.

FIG. 1 shows a laparoscopic instrument 1, which proximally possesses a handgrip 2, distally a grasper 3 and wherein a tube 4 extends between the handgrip 2 and the grasper 3, wherein coupling means are provided for operating the grasper 3 by means the handgrip 2.

In the typical manner, the grasper 3 possesses an upper jaw 5 and a lower jaw 6.

The upper jaw 5 or the lower jaw 6, or both the upper jaw 5 and the lower jaw 6 may be embodied as force sensor. Hereinbelow this embodiment will be further elucidated by way of the general schematic illustration of a force sensor according to the invention as shown in FIG. 2.

In FIG. 2 a force sensor 7 is shown, possessing a deformable body 8. This deformable body 8 consists, for example, of the upper jaw 5 or the lower jaw 6 of the grasper 3 of the laparoscopic instrument 1.

In FIG. 2 reference numeral 9 designates the hinge 9 of the laparoscopic instrument 1 in FIG. 1.

The force sensor 7 shown in FIG. 2 has a detector 10, 11 coupled with the deformable body 8 for measuring a force F brought to bear on the deformable body 8.

The just referred to detector 10, 11 comprises a light conductor 11 and, disposed close to an end 12 of the light conductor 11 and coupled with the body 8, a position-variable mirror 10, of which the light reflection depends on the position of the mirror 10 in relation to the end 12 of the light conductor 11. In this connection, the light conductor 11 is stationarily incorporated in the body 8. The light conductor 11 is preferably made of glass fibre, allowing it to be of very small dimensions such as are particularly desirable for the laparoscopic instrument 1 shown in FIG. 1.

The light conductor 11 is preferably designed for conducting light to and from the mirror 10, and possesses a processing organ symbolized by the reference numeral 13, for determining a ratio between a first amount of light conducted by the light conductor 11 to the mirror 10 and a second amount of light conducted by the light conductor 11 from the mirror 10, wherein this ratio is used as indication of the force brought to bear on the body 8. In connection with the laparoscopic instrument 1 as shown in FIG. 1, it should be observed that in a manner known to the person skilled in the art (and therefore not shown), the just referred to processing organ 13 is able to control an actuator operating the handgrip 2 for providing the user of the laparoscopic instrument 1 with a feedback signal that depends on the force measured.

For the precision of the force measured and the linearity of the force sensor according to the invention it is further desirable, for the deformable body 8 to be embodied with a channel 14 extending longitudinally in the body 8, which channel 14 exits at either side in a first recess 15 and a second recess 16, each of which recesses is in the direction at right angles to the channel 14 wider than said channel 14. This construction endows the deformable body with the property that when a force F is brought to bear to the right of the second recess 16, the deflection of the mirror 10 will be as much as possible a linear one. In order to aid this, it is desirable for the mirror 10 to be placed in the channel 14 on a mirror holder 17 that is mounted on the wall facing away from the end of the light conductor 11, i.e. the wall of recess 16. The length of the mirror holder 17 is preferably chosen such that when a force is applied to the deformable body 8, the light-reflecting surface of the mirror 10 will undergo a substantially linear deflection.

In the foregoing the invention is discussed by way of a non-limiting exemplary embodiment. The protective scope due the invention is therefore not determined by the exemplary embodiment provided, but exclusively by the appended claims. The above given elucidation merely serves to expound said claims without limiting their protective scope.

What is claimed is:

1. A force sensor comprising a deformable body and a detector coupled to this deformable body for measuring a force brought to bear on the deformable body, wherein the detector comprises a light conductor and, disposed close to an end of the light conductor and coupled with the body a position-variable mirror, the light reflection of which depends on the position of the mirror, and wherein the deformable body comprises a channel extending longitudinally in the body, exiting on both sides in a first and second recess, each of which in the direction at right angles to the channel, is wider than the channel.

2. A force sensor according to claim 1, wherein the light conductor is a glass fiber stationarily incorporated in the body.

3. A force sensor according to claim 1, wherein the light conductor is designed for conducting light to and from the mirror.

4. A force sensor according to claim 1, wherein the sensor additionally comprises a processing organ for determining a ratio between a first amount of light conducted by the light conductor to the mirror and a second amount of light conducted by the light conductor from the mirror, and wherein this ratio serves as indication of the force brought to bear on the body.

5. A force sensor according to 1, wherein the light conductor is at least partly incorporated in the channel, and exits in the channel.

6. A force sensor according to claim 1, wherein the mirror is placed in the channel, supported by a mirror holder mounted on a recess wall away from the light conductor.

7. A force sensor according to claim 6, wherein the mirror holder has a length such that when a force is brought to bear on the deformable body, the light-reflecting surface of the mirror undergoes a substantially linear deflection.

* * * * *